United States Patent
McGovern et al.

(10) Patent No.: US 10,357,390 B2
(45) Date of Patent: Jul. 23, 2019

(54) ANKLE FOOT TENSIONED ORTHOSIS

(71) Applicant: REHABILITATION INSTITUTE OF CHICAGO, Chicago, IL (US)

(72) Inventors: Donald McGovern, Western Springs, IL (US); Wesley Quigley, Joliet, IL (US)

(73) Assignee: REHABILITATION INSTITUTE OF CHICAGO, Chicago, IL (US)

(*) Notice: Subject to any disclaimer, the term of this patent is extended or adjusted under 35 U.S.C. 154(b) by 400 days.

(21) Appl. No.: 14/541,449

(22) Filed: Nov. 14, 2014

(65) Prior Publication Data

US 2016/0135978 A1 May 19, 2016

(51) Int. Cl.
*A61F 5/01* (2006.01)

(52) U.S. Cl.
CPC .... *A61F 5/0127* (2013.01); *A61F 2005/0165* (2013.01); *A61F 2005/0167* (2013.01); *A61F 2005/0179* (2013.01)

(58) Field of Classification Search
CPC .. A61F 5/00; A61F 5/01; A61F 5/0102; A61F 5/0127; A61F 2005/0165; A61F 2005/0167; A43B 5/0452; A43B 5/0454; A43B 5/0456; A43B 5/0462
USPC .............. 602/27, 28; 36/118.2, 118.4, 118.8
See application file for complete search history.

(56) References Cited

U.S. PATENT DOCUMENTS

| | | | |
|---|---|---|---|
| 5,328,444 A | 7/1994 | Whiteside | |
| 5,810,754 A | 9/1998 | Kenosh | |
| 6,083,184 A | 7/2000 | Kenosh | |
| 6,289,558 B1 | 9/2001 | Hammerslag | |
| 7,591,050 B2 | 9/2009 | Hammerslag | |
| 7,678,067 B1 | 3/2010 | Smith et al. | |
| 7,841,999 B2* | 11/2010 | Napholz | A61F 5/0123 602/16 |
| 7,950,112 B2 | 5/2011 | Hammerslag et al. | |
| 7,954,204 B2 | 6/2011 | Hammerslag et al. | |
| 7,992,261 B2 | 8/2011 | Hammerslag et al. | |
| 8,091,182 B2 | 1/2012 | Hammerslag et al. | |
| 8,235,924 B2* | 8/2012 | Bachmann | A61F 5/0102 602/16 |
| 8,277,401 B2 | 10/2012 | Hammerslag et al. | |
| 8,381,362 B2 | 2/2013 | Hammerslag et al. | |
| 8,424,168 B2 | 4/2013 | Soderberg et al. | |
| 8,468,657 B2 | 6/2013 | Soderberg et al. | |

(Continued)

FOREIGN PATENT DOCUMENTS

KR 10-2014-0104825 A 8/2014

OTHER PUBLICATIONS

Yamane, A., "Lower Limb Orthoses and Rehabilitation" in Lin, V, Cardenas, D, Cutler, N, eds., Spinal Cord Medicine: Principles and Practice, 2002, pp. 675-689, Demos Medical Publishing, New York.

(Continued)

*Primary Examiner* — Keri J Nelson
(74) *Attorney, Agent, or Firm* — Drinker Biddle & Reath LLP

(57) ABSTRACT

An orthosis for supporting a human ankle joint is described. The orthosis may include a foot section and a tibial section, with a tensioning mechanism configured to adjust the tension between the foot section and the tibial section in order to change the range of motion of the joint. Methods for assembling and using an orthosis are also described.

18 Claims, 4 Drawing Sheets

(56) References Cited

U.S. PATENT DOCUMENTS

| | | | |
|---|---|---|---|
| 8,516,662 | B2 | 8/2013 | Goodman et al. |
| 9,855,161 | B1 * | 1/2018 | Bonaroti .............. A61F 5/0102 |
| 2011/0144554 | A1 | 6/2011 | Weaver, II et al. |
| 2013/0012856 | A1 | 1/2013 | Hammerslag et al. |

OTHER PUBLICATIONS

Ossur, "Ossur OA Unloader One", Brochure P-530226, Apr. 2013, 4 pages.
Ossur, "Unloader One: Instructions for Use", Brochure IFU0556 Rev 1, 2012, 50 pages.
Ossur, "Unloader One", <http://www.ossur.com/oa-solutions/oa-products/oa-knee/custom-oa-braces/unloader-one-custom>, 2014, 3 pages.
Ossur, "Unloader One: Custom & OTS", <http://assets.ossur.com/library/15886/U1%20w%20SmartDosing%20Catalog%20Pages.pdf>, downloaded Sep. 2014, 3 pages.
Ossur, "Unloader One: Quick Reference Card", Brochure QRC 0009 EN Rev 2, 2010, 2 pages.
Orthotic Shop, "Smart Step Drop Foot AFO Brace", <www.orthoticshop.com/smart-step-drop-foot-afo-brace.html?gclid=CKrMk8HErr0CFexcMgoddT4AUg>, downloaded Nov. 18, 2014, 3 pages.
Insightful Products LLC, "Step-Smart Custom Foot & Ankle Brace Solution", <http://www.step-smart.com/>, 2004, 2 pages.
Cortex, "Corflex Soft AFO Brace for Foot Drop," <www.corflex.com/products/lower-extremity/foot-ankle/plantar-faciitis/cooltex-soft-afo/>, downloaded Nov. 18, 2014, 3 pages.
Trulife, "Sure Step Comprehensive Plantar Flexion Stop", <trulife.com/all-products/orthotics/ankle-foot-orthoses/custom/sure-step-comprehensive-plantar-flexion-stop-1>, downloaded Nov. 18, 2014, 2 pages.
Trulife, "Sure Step Comprehensive Dorsi Assist", <trulife.com/all-products/orthotics/ankle-foot-orthoses/custom/sure-step-comprehensive-dorsi-assist-1>, downloaded Nov. 18, 2014, 2 pages.
ComfySplints, "Comfy Spring Ankle Foot", <www.comfysplints.com/product_info.php?cPath=26&products_id=97>, downloaded Nov. 18, 2014, 2 pages.
Prolab Orthotics, "New Custom Functional AFO", <prolaborthotics.com/Products/AFO/NewFunctionalAFO/tabid/338/Default 2009, 1 page.

International Search Report and Written Opinion issued in related application PCT/US2015/060711, dated Jan. 20, 2016, 13 pages.

* cited by examiner

ANKLE FOOT TENSIONED ORTHOSIS

TECHNICAL FIELD

The present disclosure is generally directed to ankle orthotic devices and, more particularly, to an ankle foot tensioned orthosis.

BACKGROUND

Ankle Foot Orthoses ("AFO") and Knee Ankle Foot Orthoses ("KAFO") are orthotic braces that limit motion at the ankle joint or knee joint of a child or adult. Limiting motion helps stabilize the joint, which helps patients recover from a variety of debilitating diseases and injuries such as cerebral vascular accident, cerebral palsy, traumatic brain injury, spinal cord injury, or genu recurvatum. As the patient's recovery progresses, a physician or other practitioner may recommend that the patient be given more control over his or her joint motion as function improves. Alternately, the amount of joint control a patient wishes to have may depend on the type of activity the patient in which the patient wishes to engage. For instance, a child patient may want more joint control to run around and play on a playground and less joint control and more stability while in the classroom.

The changing joint control needs of a patient in recovery often result in patients using more than one orthotic device during recovery. The use of multiple orthotics increases health care costs and requires the patient to take time away from his or her schedule for multiple appointments. One currently-available type of AFO is a plastic solid ankle foot orthosis ("SAFO"), which is worn on the user's ankle and eliminates most ankle motion. This system provides increased stability but greatly limits the patient's ability to move his or her ankle Another currently-available AFO allows free ankle dorsiflexion with a plantarflexion stop, which limits ankle plantarflexion. (Dorsiflexion is the flexion of the ankle where the angle between the foot and shin decreases. Plantarflexion is the extension of the ankle where the angle between the foot and the shin increases.) AFOs having joints with adjustable stops are available, but require the clinician to set the range of motion available to the patient, which the patient cannot alter. In addition, such joints add weight and bulk to a device which impairs the patient's ability to wear a shoe over the AFO.

DRAWINGS

While the appended claims set forth the features of the present techniques with particularity, these techniques may be best understood from the following detailed description taken in conjunction with the accompanying drawings of which:

DESCRIPTION

Figure 1:
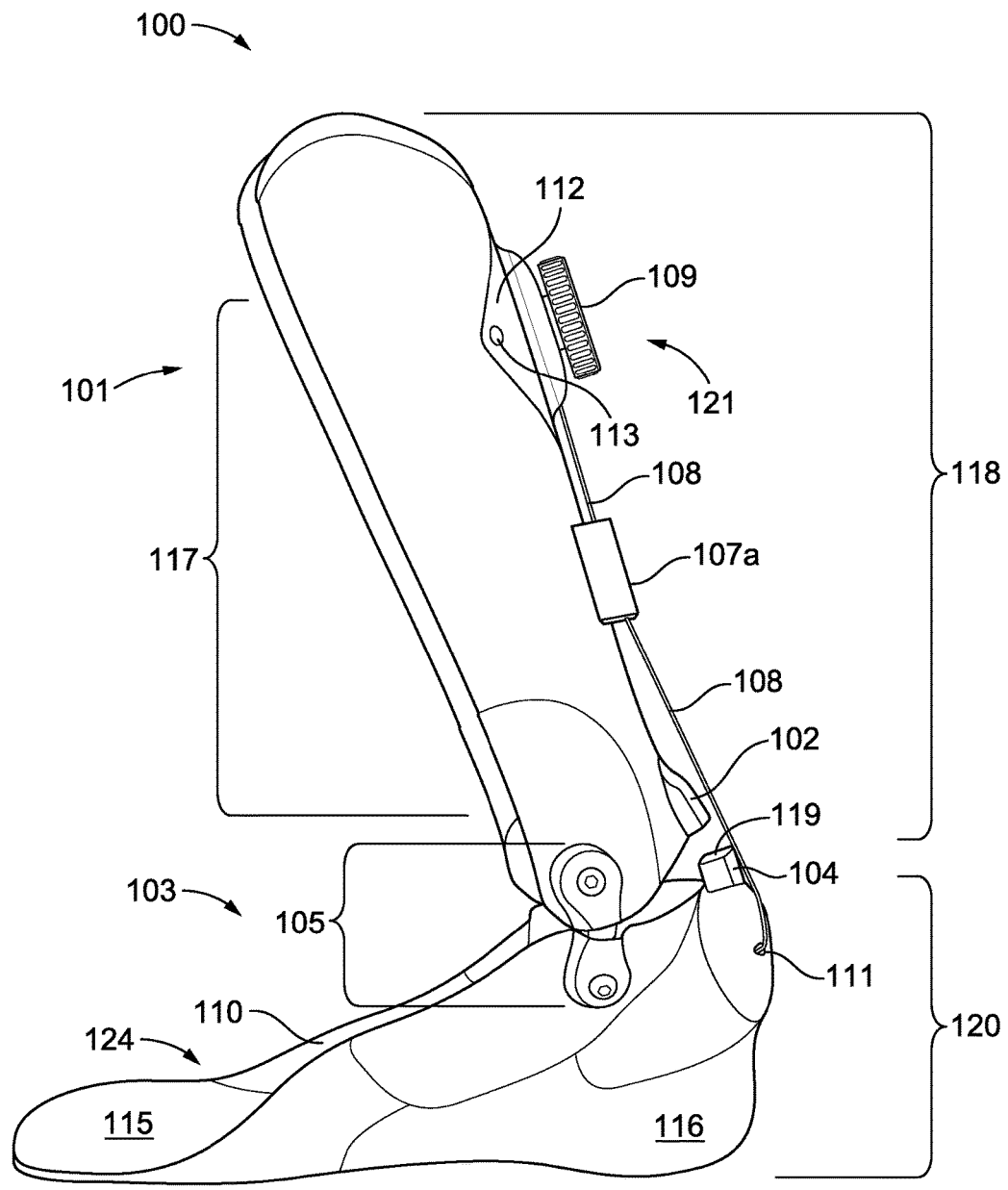
FIG. 1 is a side view of an embodiment of an ankle foot orthosis.

Turning to the drawings, wherein like reference numerals refer to like elements, techniques of the present disclosure are illustrated as being implemented in a suitable environment. The following description is based on embodiments of the claims and should not be taken as limiting the claims with regard to alternative embodiments that are not explicitly described herein.

Disclosed herein is an orthosis for supporting a human ankle joint. In an embodiment, the orthosis comprises a foot section configured to don to a foot distal to the joint; a tibial section configured to don to a crus proximal to the joint; and a tensioning mechanism attached to the foot section and to the tibial section and configured to adjust the tension between the foot section and the tibial section in order to change the range of motion of the joint.

Also disclosed is a method for assembling an orthosis for supporting a human ankle joint. In an embodiment, the method comprises attaching a foot section to a tibial section by a pivoting mechanism that allows the tibial section to pivot with respect to the foot section and connecting a tensioning mechanism between the tibial section and a posterior foot region.

A method of using an orthosis configured to support a human ankle joint is also disclosed. In an embodiment, the method comprises donning a foot section of an orthosis to a foot distal to the joint; donning a tibial section of the orthosis to a crus proximal to the joint; connecting a tensioning mechanism between the tibial section and the foot section; and making at least one adjustment to the tensioning mechanism, each adjustment either increasing or decreasing the range of motion available to the joint; wherein an adjustment of the tensioning mechanism does not require removal of the foot section from the foot or removal of the tibial section from the crus.

Various embodiments of the present disclosure include a therapeutic orthosis that can be donned, or worn, on, the joint of a child or adult. In an embodiment, the article comprises an AFO. In another embodiment, the article comprises a knee orthotic ("KO").

Concepts related to the orthoses are discussed with reference to varying amounts of joint motion needed at various times of therapy. The orthoses may provide complete support, substantial support, or minimal support to the patient's joint, depending on the configuration of the orthosis.

Concepts related to the orthoses are also discussed with reference to the position of the articulating limb members relative to the user's body. With respect to two limb members connected by an anatomical joint, the limb member that is relatively closer to the user's center is "proximal" and the limb member that is relatively further from the user's center is "distal." For example, the ankle joint is attached to the foot on the distal side of the joint and to the lower leg (called the "crus") on the proximal side of the joint. With respect to the ankle joint, the foot is the distal limb member and the crus is the proximal limb member.

In certain embodiments disclosed herein, the orthosis provides joint stability and flexibility that is adjustable by a user. The user can adjust the amount of stability or flexibility provided by the orthosis quickly and without the assistance of a clinician or another person.

In certain embodiments disclosed herein, the orthosis can provide adjustable support of the joint. The orthosis can provide complete support that prevents joint flexion or extension under ordinary conditions; substantial support that allows limited flexion or extension motion under ordinary conditions, adjustable in one degree increments; or minimal support that allows up to fifteen degrees of free flexion or extension. The adjustable support allows a patient or other user to participate in a much wider range of functional activities with a single device, in the case of the ankle orthosis, without donning alternative foot wear.

An embodiment of an ankle orthosis is shown in FIG. 1. AFO 100 comprises tibial section 101 that includes a tibial stop 102 and a foot section 103 that includes a foot stop 104. In the embodiment shown in FIG. 1, the tibial section 101 serves as the proximal component of the AFO 100 and the foot section 103 serves as the distal component of the AFO 100. The AFO 100 may be donned on the ankle joint of the user. The tibial section 101 may be donned to the user's tibia, or crus, and the foot section 103 may be donned to the user's foot. The tibial section 101 and the foot section 103 are mechanically connected by a hinge 105, which allows the foot section 103 to dorisflex or plantarflex relative to the tibial section 101, thus allowing the user's ankle to dorsiflex or plantarflex, respectively. The foot section 103 and the tibial section 101 are further mechanically connected by a tensioner 121. The tensioner 121 may comprise, for example, a tension knob 109 and a cable 108. The cable 108 is substantially inelastic. In one embodiment, tightening the tensioner 121 reduces the length of the cable 108 and causes the foot section 103 to plantarflex relative to the tibial section 101. The resulting reduction in the dorsiflexion range of motion leads to either complete support, substantial support, or minimal support of the user's joint. Loosening the tensioner 121 increases the length of the cable 108 and loosens the mechanical connection between the foot section 103 and the tibial section 101 so that the user can dorsiflex the joint more freely.

The AFO 100 may be made of plastic or another suitable material that supports the ankle. The tibial section 101 and the foot section 103 are further divided into more general regions. The tibial section 101 may include a posterior tibial region 118 as well as an anterior tibial region 117. The foot section 103 may include a foot plate 115 that has a designated space for the user's weight, a heel region 116, a posterior foot region 120, an anterior foot region 124, and side walls 110. The anterior foot region 124 is generally defined as the portion of the foot section 103 anterior to (in other words, in front of) the connection to the tibial section 101, and the posterior foot region 120 is generally defined as the portion of the foot section 103 posterior to (in other words, behind) the connection to the tibial section 101. In one embodiment, the connection between the foot section 103 and the tibial section 101 is accomplished via a hinge 105. In an embodiment, the side walls 110 may be adjustable. For example, as the user gains strength, a practitioner may trim material away from the side walls 110 to allow for greater flexibility in the foot section 103. Additionally, the foot plate 115 may be adjusted. For example, it may be thinned, e.g., by grinding the material, in order to increase flexibility of the foot section 103 in the area of the user's toe joints.

Tibial Section.

The tibial section 101 is the portion of the AFO 100 that is donned on the user's leg. In one embodiment, the tibial section 101 fits from the user's ankle up towards the user's calf before the knee. The tibial section 101 may encircle the calf of a patient's leg. The anterior tibial region 117 may be open so that the patient's leg is not entirely encased in the tibial section 101 of the AFO 100. In other embodiments, the AFO 100 may be designed such that the proximal anterior area of the user's tibia will be encased for greater support to the user. The tibial section 101 may be attached to the user's leg by a strap (not shown) connected across the opening of anterior tibial region 117 or by other fastening methods.

Foot Section.

The foot section 103 is the portion of the AFO 100 that is donned on the user's foot. The foot section 103 fits the user's foot from the front area of the foot (including the toes and joints connecting the metatarsals with the phalanges) through the user's midfoot arch region to the user's heel. The foot plate 115 forms the sole of the foot section 103. The user's foot rests on the foot plate 115 when the user dons AFO 100. The rear of the foot section 103 is the heel region 116, which receives the user's heel. The foot section 103 may be made of, among other materials, polypropylene, a more flexible copolymer plastic, or more rigid carbon graphite or pre-impregnated carbon fiber materials.

In an embodiment, the foot section 103 does not fully encase the foot. As shown in FIG. 1, the anterior foot region 124 is open, leaving the top of the user's foot exposed. The foot plate 115 may have a predominately flat surface, on which the bottom of the user's foot may rest. Alternately, the foot plate 115 may be molded to fit the shape of the sole of a particular user's foot. In one embodiment, shown in FIG. 1, the foot section 103 includes side walls 110 located to the anterior of the hinge 105 and near each side of the hinge 105. The side walls 110 may partially encase the user's ankle and heel. The partial encasing of the foot at and around the heel region 116 can assist in providing stability to the user's ankle. The anterior tibial region 117 and the anterior foot region 124 leave the foot and leg exposed to the environment. This also allows the user to don the AFO 100 more easily and reduces the size and bulk of the AFO 100 that is inserted into the user's shoe.

Hinge.

Figure 2:
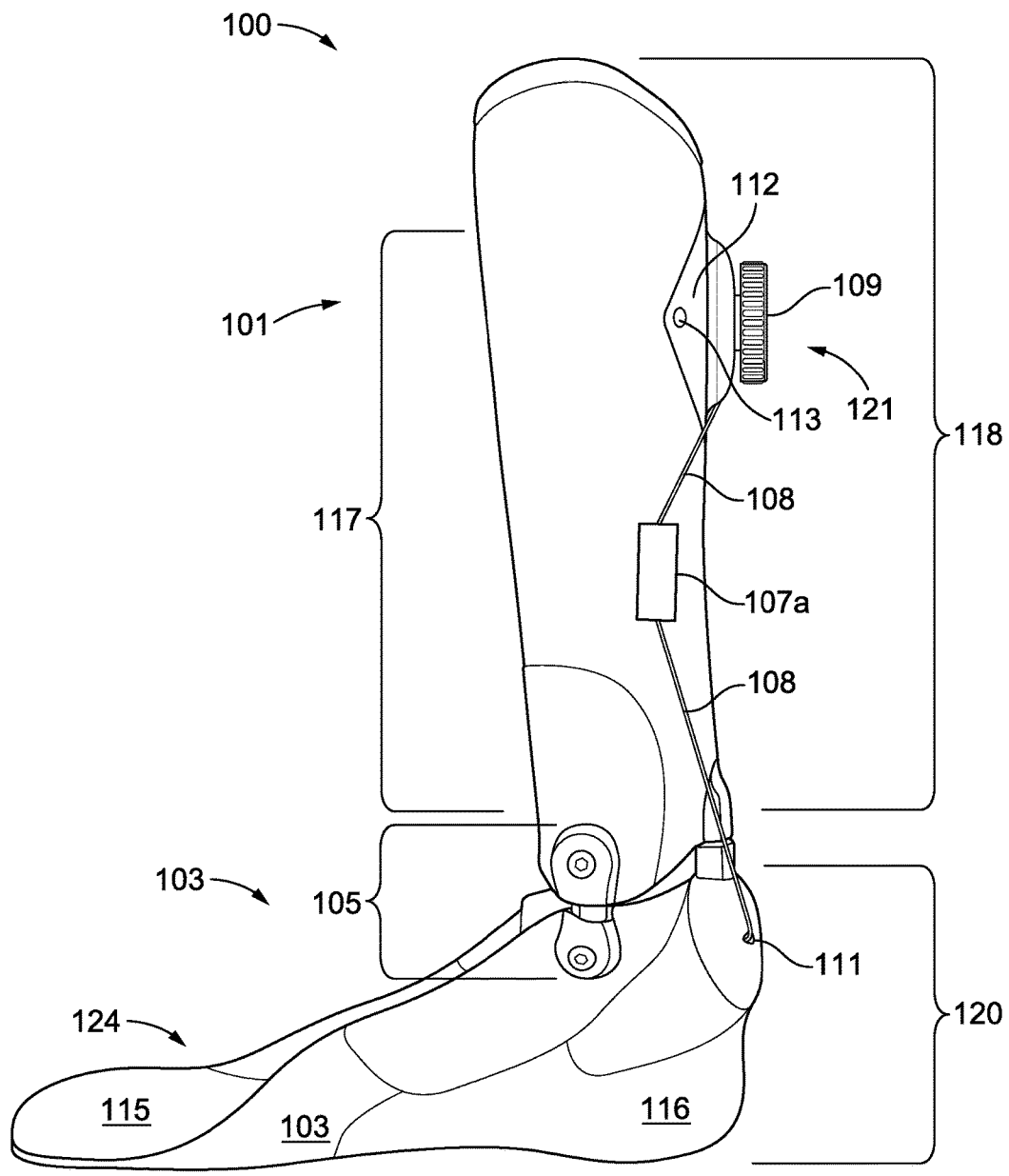
FIG. 2 is another side view of an embodiment of an ankle foot orthosis.

As shown in FIG. 1, tibial section 101 and foot section 103 connect at hinge 105. In one embodiment, hinge 105 is a metal-free motion ankle joint manufacture which contributes to the AFO's 100 increased support and stability and also assists in making AFO lightweight. Metal joints can also be used instead, if greater rigidity is desired. As shown in FIG. 2, the hinge 105 allows for dorsiflexion or plantarflexion of foot section 103 along an axis of rotation 106 (also shown in FIG. 3). In an embodiment, the AFO 100 comprises a stop for limiting motion of the foot section relative to the tibial section. The stop may comprise a first stop portion on the posterior foot region and a second stop portion on the tibial section. As shown in FIG. 2, a first stop portion, foot stop 104, is located directly above the heel region 116 on the posterior region of the foot section 103, and the tibial stop 102 is located on the posterior tibial region 118 towards the bottom of the tibial section 101. The foot stop 104 and the tibial stop 102 engage along a stop edge 119, which inhibits further plantarflexion of the tibial section 101 relative to the foot section 103.

Tensioner.

The tensioner 121 may be used to provide adjustable tension between the tibial section 101 and the foot section 103. In the embodiment shown in FIG. 1, the tension knob 109 is coupled to the upper portion of the tibial section 101. The tensioner 121 also includes a first tension guide 107A and a second tension guide 107B. The tension knob 109 is disposed above the first and second cable guides 107A and 107B. The tension knob 109 may be turned to shorten the length of the cable 108. The tension on the cable 108 tends to resist dorsiflexion of the foot section 103. Increased tension on the cable 108 pulls on a cable housing 111, causing the foot section 103 to plantarflex by pivoting about the axis 106. Loosening the tensioner 121 allows for a greater range of motion of the foot section 103 relative to the tibial section 101. When the cable 108 is substantially inelastic, the tensioner 121 reduces the range of dorsiflexion of the user's ankle by reducing the active length of the cable 108.

Figure 4:
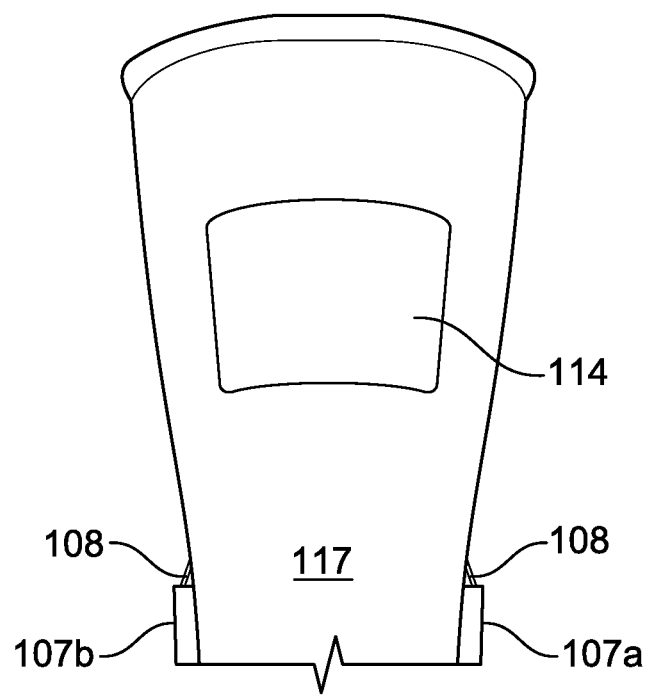
FIG. 4 is an anterior view of an embodiment of an ankle foot orthosis.

In an embodiment, a user can adjust the tension knob 109 to control the amount of tension in the cable 108. One embodiment of the tensioner 121, shown in FIG. 4, is a Boa Closure System offered by Boa Technology Inc. (Denver, Colo.). The cable 108 is shortened by rotating the tension knob 109 in a clockwise direction. For example, as the tension knob 109 is rotated, the length of the cable 108 that passes from the knob 109 through the first tension guide 107A, the cable housing 111, and the second tension guide 107B, is reduced. The cable housing 111 may be considered to be a guide. Shortening the cable 108 increases the tension applied between the tibial section 101 and the foot section 103. The cable 108 is lengthened by releasing tension knob 109.

When tension knob 109 is pressed inward and turned counter-clockwise, tension on the cable 108 increases. Increased tension on the cable 108 causes the foot section 101 to plantarflex relative to the tibial section 103 until the foot section 101 and the tibial section 103 engage along the stop edge 119, which limits or prevents allowable dorsiflexion of the user's ankle joint.

When the tension knob 109 is pulled out, an internal ratchet lock (not shown) in tensioner 121 is unlocked, which reduces tension on cable 108. Reduced tension on the cable 108 loosens the mechanical connection between the foot section 101 and the tibial section 103, allowing the user increased dorsiflexion of his or her ankle joint. The tensioner 121 is one example of a length adjusting mechanism. Other length adjusting mechanisms are known in the art.

Placement of Tensioner.

Figure 3:
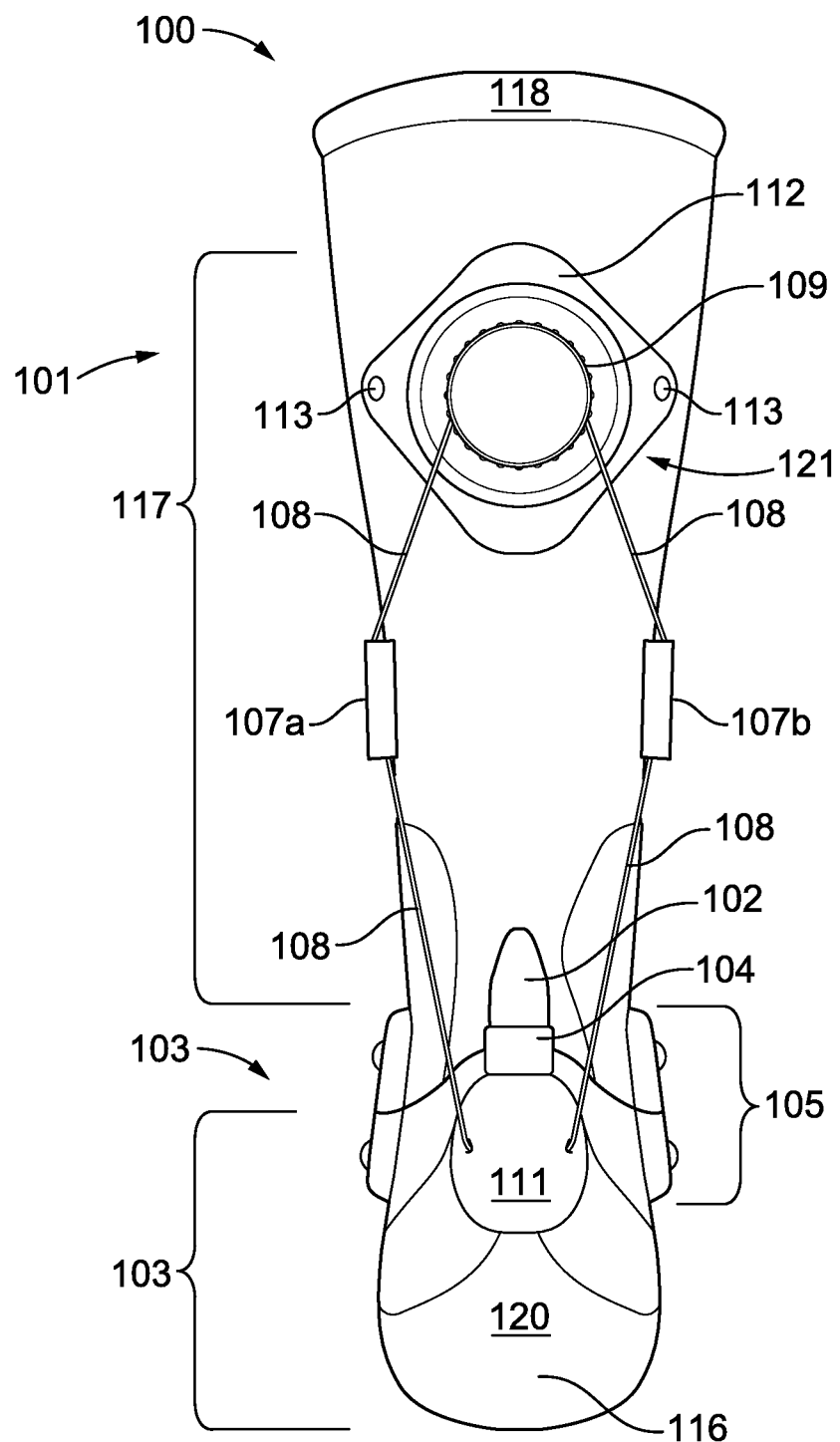
FIG. 3 is a posterior view of an embodiment of an ankle foot orthosis.

In an embodiment, shown in FIGS. 1-3, the tensioner 121 is attached to the posterior tibial region 118 of the tibial section 101. The housing 112 may cover the attachment of the tensioner 109 to the tibial section 101. The housing 112 may be coupled to the tibial section 101 by screws 113.

Threading of Cable.

As shown in FIG. 3, the cable 108 may be threaded from the cable housing 111, through the first cable guide 107A, through the tensioner 121, through the second cable guide 107B, and back to the cable housing 111. The cable guides 107A and 107B may be molded plastic or other appropriate material, or may be part of the tibial section 101. In an embodiment, the cable guides 107A and 107B are located on opposite sides of the tibial section 101. The cable housing 111 may be located on the posterior foot region 120 under the foot stop 104. The cable housing 111 anchors cable 108 onto the foot section 103.

FIG. 4 discloses the anterior tibial region 117 of the tibial section 101. In one embodiment, a covering material 114 may cover the attachment of the tensioner 121 to the tibial section 101, so that the user's limb is not scratched or otherwise irritated and to discourage a user from tampering with the tensioner 121, which may damage or impair the AFO 100.

In another embodiment, the AFO 100 may be sized to specifically accommodate the limb of a child. For instance, the foot section 101 and the tibial section 103 may be manufactured using a custom mold made by an impression or a computer scan of the patient's limb.

The AFO 100 may be manufactured as a series of components for assembly. For instance, the tibial section 101, the foot section 103, the hinge 105, and/or the tensioning mechanism 121 may be manufactured as individual components. Components, other than the foot section 101 (e.g., as custom manufactured) and the tibial section 103 may be offered for sale in the same kit or in different kits. In an embodiment, a kit may include multiple cables 108 of different lengths. The clinician would select the most appropriately sized cable 108 for the particular patient to aid in the custom fabrication of an AFO 100 on an individual patient limb. The clinician may assemble the AFO 100 as described herein. It is also possible to provide kits with the tibial section 101 and foot section 103 (either of which may be off-the-shelf and pre-sized).

A method to assemble such an orthosis is now described. The clinician prepares the foot section 102 and the tibial section 104. These may be prepared, for instance, using custom molds of the patient's limbs. The clinician attaches the foot section 102 to the tibial section 104 by a pivoting mechanism, such as the hinge 105, which allows the tibial section 104 to pivot with respect to the foot section 102. The clinician connects the tensioning mechanism, such as the tensioning mechanism 121, between the tibial section 102 and a posterior region of foot section 102. For instance, the clinician may attach the length adjusting mechanism (e.g., the tensioner 121) to the tibial section 104. The clinician also may insert the cable 108 through a first guide on the posterior foot region, such as the cable housing 111, a second guide on the tibial section, such as the tension guide 107a, and a third guide on the tibial section, such as the tension guide 107a. The clinician completes the connection of the cable 108 to the tensioning mechanism 121 and then adjusts the length of cable 108 for initial use by the patient.

In view of the many possible embodiments to which the principles of the present discussion may be applied, it should be recognized that the embodiments described herein with respect to the drawing figures are meant to be illustrative only and should not be taken as limiting the scope of the claims. Therefore, the techniques as described herein contemplate all such embodiments as may come within the scope of the following claims and equivalents thereof.

We claim:

1. An orthosis for supporting a human ankle joint, the orthosis comprising:
    a foot section configured to don to a foot distal to the joint;
    a tibial section configured to don to a crus proximal to the joint;
    a tensioning mechanism attached to the foot section and to the tibial section, the tensioning mechanism comprising
        a cable,
        a tensioner configured to reduce or increase the length of the cable, thereby adjusting the amount of tension on the cable and the range of motion of the joint, the tensioner positioned on an upper posterior region of the tibial section, and
        a cable housing positioned on a posterior region of the foot section and through which the cable passes,
        wherein the tension applied by the tensioning mechanism is distributed along the posterior regions of the orthosis.

2. The orthosis of claim 1, wherein the foot section comprises a posterior foot region configured to be coupled to the tension mechanism.

3. The orthosis of claim 2, wherein the cable is an inelastic cable that couples the tibial section to the posterior foot region.

4. The orthosis of claim 1, wherein the tibial section comprises a first cable guide and a second cable guide to route the cable, the first cable guide and the second cable guide being positioned on opposite sides of the tibial section.

5. The orthosis of claim 4, wherein the orthosis comprises a stop for limiting motion of the foot section relative to the tibial section.

6. The orthosis of claim 5, wherein the stop comprises a first stop portion on the posterior foot region and a second stop portion on the tibial section.

7. The orthosis of claim 6, wherein the foot section comprises a side wall made of a removable material.

8. The orthosis of claim 7, wherein the foot section and the tibial section are configured to be attached by a hinge.

9. A method for assembling an orthosis for supporting a human ankle joint, comprising:
    attaching a foot section to a tibial section by a pivoting mechanism that allows the tibial section to pivot with respect to the foot section; and
    connecting a tensioning mechanism between the tibial section and a posterior foot region, wherein the tensioning mechanism comprises
        a cable that couples the tibial section to the posterior foot region,
        a tensioner configured to reduce or increase the length of the cable, thereby adjusting the amount of tension on the cable and the range of motion of the joint, the tensioner positioned on an upper posterior region of the tibial section, and
        a cable housing positioned on the posterior region of the foot section and through which the cable passes,
    wherein the tension applied by the tensioning mechanism is distributed along the posterior regions of the orthosis.

10. The method of claim 9, where the connecting the tensioning mechanism comprises attaching the tensioner to the tibial section.

11. The method of claim 10, wherein connecting the tensioning mechanism further comprises inserting the cable through a first guide on the posterior foot region, a second guide on the tibial section, and a third guide on the tibial section.

12. The method of claim 11, further comprising selecting the cable from a plurality of cables of different lengths.

13. The method of claim 10, further comprising:
    molding the foot section from a plastic material; and
    molding the tibial section from a plastic material.

14. The method of claim 10, further comprising adjusting the tensioner to provide an initial tension on the orthosis.

15. A method of using an orthosis configured to support a human ankle joint, comprising:
    donning a foot section of an orthosis to a foot distal to the joint;
    donning a tibial section of the orthosis to a crus proximal to the joint;
    connecting a tensioning mechanism between the tibial section and the foot section, wherein the tensioning mechanism comprises
        a cable,
        a tensioner configured to reduce or increase the length of the cable, thereby adjusting the amount of tension on the cable and the range of motion of the joint, the tensioner positioned on an upper posterior region of the tibial section, and
        a cable housing positioned on a posterior region of the foot section and through which the cable passes; and
    making at least one adjustment to the tensioner, each adjustment either increasing or decreasing the length of the cable, thereby increasing or decreasing the range of motion available to the joint,
    wherein an adjustment of the tensioner does not require removal of the foot section from the foot or removal of the tibial section from the crus, and
    wherein the tension applied by the tensioning mechanism is distributed along the posterior regions of the orthosis.

16. The method of claim 15, wherein the at least one adjustment comprises at least one adjustment for increasing the range of motion and at least one adjustment for decreasing the range of motion.

17. The method of claim 16, wherein each adjustment adjusts the range of motion in one degree increments.

18. The method of claim 15, wherein connecting a tensioning mechanism comprises connecting the tensioning mechanism between the tibial section and the posterior region of the foot section.

* * * * *